(12) United States Patent
Munro et al.

(10) Patent No.: US 9,622,712 B2
(45) Date of Patent: *Apr. 18, 2017

(54) METHOD OF DETECTING MOVEMENT BETWEEN AN IMPLANT AND A BONE

(75) Inventors: Chad R. Munro, Mabou (CA); Richard W. Van Der Put, Little Judique (CA); Andreas Burger, Mabou (CA)

(73) Assignee: Halifax Biomedical Inc., Mabou, Nova Scotia (CA)

( * ) Notice: Subject to any disclaimer, the term of this patent is extended or adjusted under 35 U.S.C. 154(b) by 787 days.

This patent is subject to a terminal disclaimer.

(21) Appl. No.: 13/818,826

(22) PCT Filed: Aug. 25, 2011

(86) PCT No.: PCT/CA2011/000967
§ 371 (c)(1), (2), (4) Date: Sep. 6, 2013

(87) PCT Pub. No.: WO2012/024783
PCT Pub. Date: Mar. 1, 2012

(65) Prior Publication Data
US 2013/0338492 A1    Dec. 19, 2013

Related U.S. Application Data

(60) Provisional application No. 61/376,916, filed on Aug. 25, 2010.

(51) Int. Cl.
*A61B 5/103* (2006.01)
*A61B 6/02* (2006.01)
(Continued)

(52) U.S. Cl.
CPC .............. *A61B 6/022* (2013.01); *A61B 6/486* (2013.01); *A61B 6/505* (2013.01); *A61B 6/5229* (2013.01);
(Continued)

(58) Field of Classification Search
CPC ........................ A61B 19/54; A61F 2002/3008
See application file for complete search history.

(56) References Cited

U.S. PATENT DOCUMENTS

| 4,349,498 A | 9/1982 | Ellis et al. |
| 2002/0111694 A1 | 8/2002 | Ellingsen et al. |

(Continued)

*Primary Examiner* — Elmer Chao
(74) *Attorney, Agent, or Firm* — Dorsey & Whitney LLP

(57) ABSTRACT

A method of measuring the relative position of a bone implant within a bone in a patient to detect movement between the implant and bone is provided, wherein one or more radiopaque bone markers have been implanted into the bone through a cannulated implant within the bone and one or more radiopaque implant markers have been implanted into the implant. The method comprises: i) determining a first relative position of the bone marker to the implant marker under a first parameter; and ii) determining a second relative position of the bone marker to the implant marker under a second parameter, wherein a change in the position of the bone marker relative to the implant marker from the first relative position to the second relative position is indicative of movement of either the implant or the bone.

16 Claims, 7 Drawing Sheets

(51) Int. Cl.
*A61B 6/00* (2006.01)
*A61B 6/12* (2006.01)
*A61B 17/70* (2006.01)
*A61B 17/86* (2006.01)
*A61F 2/46* (2006.01)
*A61B 90/00* (2016.01)

(52) U.S. Cl.
CPC ........... *A61B 90/39* (2016.02); *A61B 6/12* (2013.01); *A61B 17/7032* (2013.01); *A61B 17/864* (2013.01); *A61B 2090/061* (2016.02); *A61B 2090/0812* (2016.02); *A61B 2090/3904* (2016.02); *A61B 2090/3916* (2016.02); *A61B 2090/3966* (2016.02); *A61B 2090/3987* (2016.02); *A61F 2002/4658* (2013.01)

(56) References Cited

U.S. PATENT DOCUMENTS

| | | | |
|---|---|---|---|
| 2005/0020913 A1 | 1/2005 | Georg et al. | |
| 2008/0269898 A1* | 10/2008 | Carls | A61B 17/7062 623/17.11 |
| 2010/0042167 A1* | 2/2010 | Nebosky | A61B 17/7061 606/315 |
| 2010/0063550 A1 | 3/2010 | Felix et al. | |

* cited by examiner

A

B

A

B

METHOD OF DETECTING MOVEMENT BETWEEN AN IMPLANT AND A BONE

This application is a 371 national stage application of PCT Patent Application No. PCT/CA2011/000967, filed Aug. 25, 2011, entitled "A Method of Detecting Movement Between an Implant and a Bone," which claims priority to U.S. Provisional Application No. 61/376,916, filed Aug. 25, 2010, the content of all of which is hereby incorporated in its entirety by reference.

FIELD OF THE INVENTION

The present invention relates generally to the field of orthopedics, and in particular, to bone implants and the use of bone implants in imaging methods.

BACKGROUND

In orthopedics there is value in determining the relative motion of two or more rigid bodies such as bone segments and bone implants. X-ray imaging is generally used to determine relative position and orientation of bone structures and implants. Radiostereometric analysis or roentgen stereophotogrammetric analysis (RSA) is a method of obtaining two simultaneous x-ray exposures of the same implant/bone structure to determine the relative positions between multiple bone segments, between bone and implant, or between multiple implants.

The use of RSA requires the implantation of radiopaque markers into the bone. Markers are currently implanted during surgery; however, this process can be time consuming. In addition, the surgical implantation of markers generally does not necessarily provide the desired accuracy. Accurate positioning of these markers improves the motion analysis results.

Accordingly, there is a need for a method which overcomes one or more of the disadvantages associated with radiopaque markers in bone for imaging purposes.

SUMMARY OF THE INVENTION

A novel method for measuring relative position of a bone implant is provided, and is useful to detect movement of an implant within a bone.

Thus, in one aspect, a method of measuring the relative position of a bone implant within a bone in a patient to detect movement between the implant and bone is provided wherein one or more radiopaque bone markers have been implanted into the bone through a cannulated implant within the bone and one or more radiopaque implant markers have been implanted into the implant. The method comprises:

i) determining a first relative position of the bone marker to the implant marker under a first parameter; and ii) determining a second relative position of the bone marker to the implant marker under a second parameter, wherein a change in the position of the bone marker relative to the implant marker from the first relative position to the second relative position is indicative of movement of either the implant or the bone.

In another aspect, a method of measuring the relative position of a first bone site to a second bone site in a patient to detect movement between the two bone sites is provided wherein one or more radiopaque bone markers have been implanted into the first bone site through a cannulated first implant within the first bone site, one or more radiopaque implant markers have been implanted into the first implant, one or more radiopaque bone markers have been implanted into the second bone site through a cannulated second implant within the second bone site and one or more radiopaque implant markers have been implanted into the second implant. The method comprises the steps of:

i) when the bone and implant markers at the first bone site are determined to be stable relative to one another, and the bone and implant markers at the second bone site are determined to be stable relative to one another, determining a first relative position of the bone and implant markers at the first bone site to the bone and implant markers at the second bone site under a first parameter; and ii) determining a second relative position of the bone and implant markers at the first bone site to the bone and implant markers at the second bone site under a second parameter, wherein a change between the first relative position and the second relative position is indicative of movement between the first and second bone sites.

In another aspect of the invention, a biocompatible plug comprising at least one radiopaque marker, wherein the marker is in a fixed position within the plug.

These and other aspects of the invention will become apparent in the detailed description that follows by reference to the figures.

DETAILED DESCRIPTION OF THE INVENTION

A method to detect movement between a cannulated bone implant and a bone in a patient is provided by measuring the relative position of the bone, in which one or more radiopaque bone markers have been implanted through the implant within the bone and one or more radiopaque implant markers have been implanted into the implant. The method comprises determining a first relative position of the bone marker to the implant marker under a first parameter; and determining a second relative position of the bone marker to the implant marker under a second parameter, wherein a change in the position of the bone marker relative to the implant marker from the first relative position to the second relative position is indicative of movement of either the implant or the bone.

In order to conduct the present method, one or more radiopaque markers are implanted into the bone through a cannulated implant within the bone. The use of a cannulated implant provides a means of delivering one or more bone markers into the bone. As one of skill in the art will appreciate, bone implants may be introduced over a guidewire that is already placed in the patient. Removal of the guide wire yields a straight void or canal through the implant that goes into the adjacent bone. The use of a needle or piston will also ensure straight insertion of a marker through the cannulated implant, whether or not a guidewire was previously used. The presence of the canal, thus, facilitates the insertion of bone markers into the bone without any additional trauma or risk of trauma to the patient. The presence of the canal also prevents bone, nerve or tissue damage, and the chance of inducing undesirable bone segment motion. The placement of the bone markers is, thus, safe. In addition, the position of the bone markers is defined since the canal is straight and of a defined depth.

Figure 1:
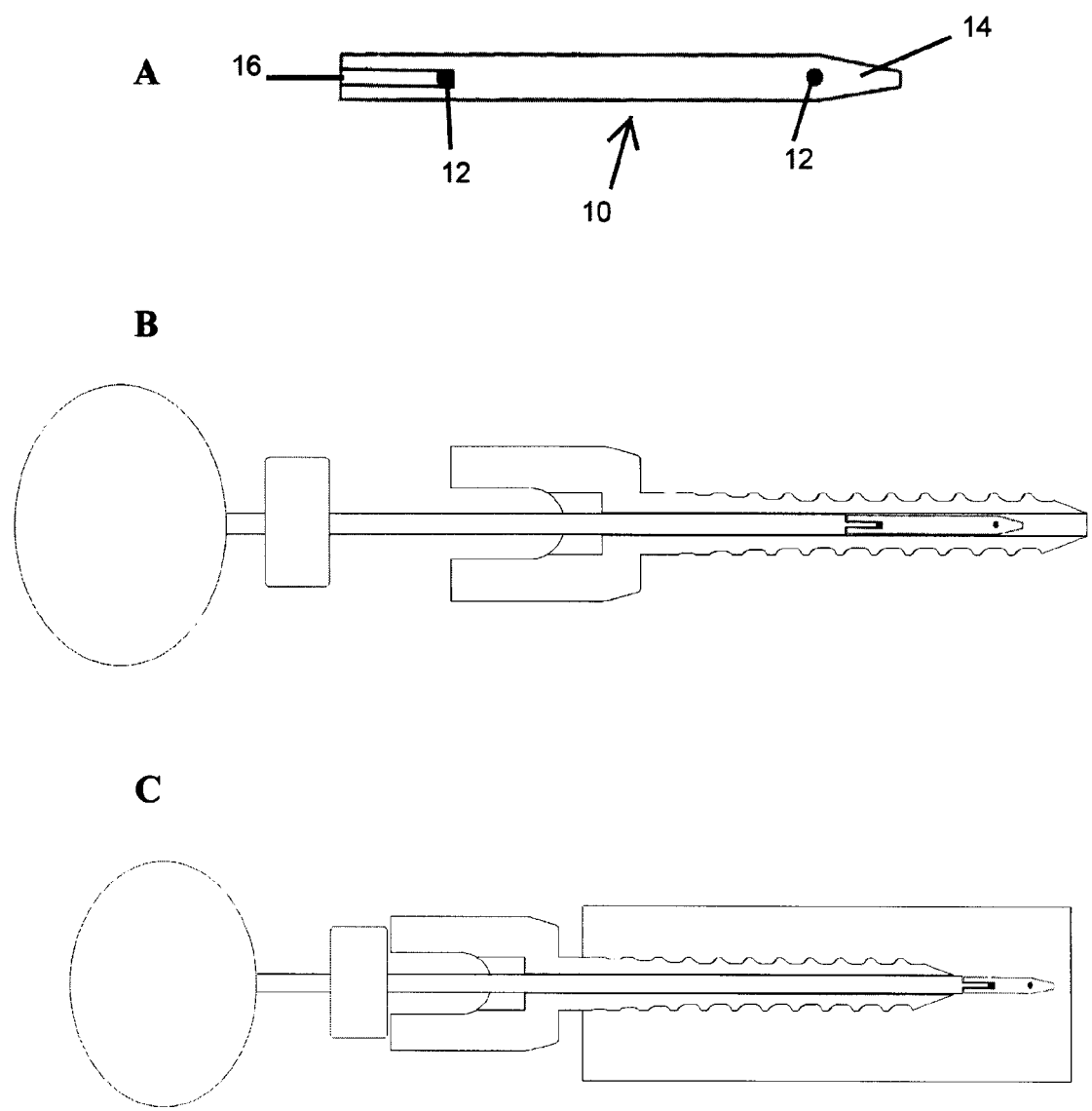
FIG. 1 illustrates a bone plug (A) and insertion of a bone plug into bone via a cannulated implant (B,C)
Figure 2:
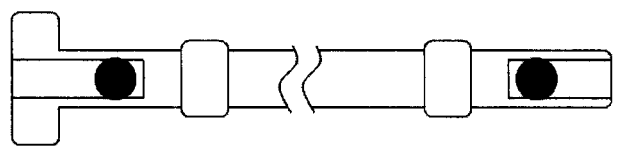
FIG. 2 illustrates an implant plug (A) and insertion of the implant plug into an implant (B)
Figure 2:
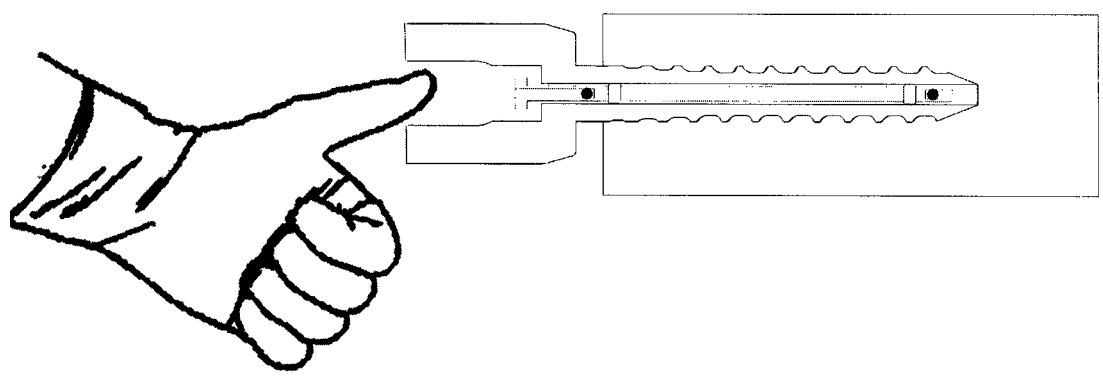

The canal of the implant provides a pathway for the bone marker, for a needle to deliver the bone marker, or for a carrier, such as a plug, which includes one or more embedded bone markers. Suitable bone markers for use in the present method include markers that can readily be detected in bone, such as radiopaque bone markers, such as tantalum or titanium markers, which may be in the form of a bead, in any suitable shape such as spherical, elongated, cubic, etc., or a wire. The radiopaque marker is pushed through the canal of the implant, generally using a needle or other instrument for this purpose, and is implanted into the bone as shown in FIG. 1. Two or more radiopaque markers may be introduced into the bone in this manner.

The bone marker may be embedded in a carrier, for example, in the form of a plug 10, which is implanted into the bone, as shown in FIG. 1A. The bone plug 10 may be made from any suitable biocompatible material such as biocompatible polymers known in the art, for example, polyethylene ethylene ketone (PEEK), POM and the like, or other radiolucent materials such as ceramic or titanium, and may contain one or multiple radiopaque markers 12. The location of the markers within the bone plug is pre-determined and the markers are fixed within the bone plug so that the relative positions between markers does not change over time. The bone plug has a shape and diameter that enables it to pushed through the canal of the target cannulated bone implant and embedded into the bone, e.g. an elongated shape. The anterior end 14 of the bone plug may be tapered to facilitate its implant into bone. The bone plug 10 may also include a channel 16 formed at its posterior end to accommodate a piston (pushing rod) to facilitate insertion of the bone plug into an implant.

The bone plug may be made using standard injection molding techniques. In this regard, the markers may be embedded within the plug during the formation of the plug using injection molding to fix the position of the markers within the plug. Alternatively, the plug may be formed with voids during the molding process into which the markers can subsequently be press-fitted.

Figure 6:
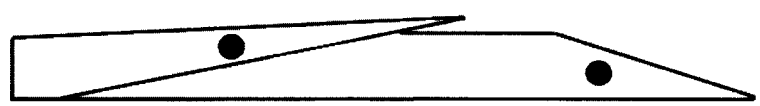
FIG. 6 illustrates a 2-piece segmented bone plug (A) which segments on implantation into bone (B)
Figure 6:
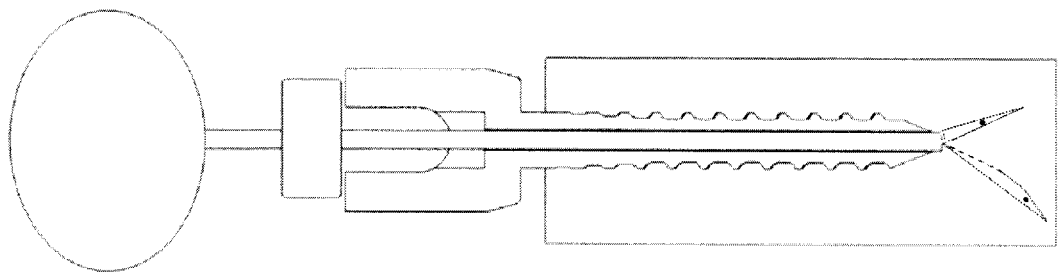

Different variations of the bone plug may exist. As indicated above, the bone plug may contain one or more markers. If the bone plug comprises more than two markers, the configuration of the markers within the plug may be collinear or non collinear. Non collinear markers in a single bone plug may provide 3D representation of the bone, provided that these markers are utilized in conjunction with an implant that also has markers in a non collinear configuration. The bone plug may comprise a single unitary segment, or may alternatively comprise multiple segments that separate on delivery to the bone, as shown in FIG. 6, and thus, assume different locations within the bone to provide a 3D representation of the bone.

To ensure that the bone plug does not move relative to the bone over time, the plug is adapted to be fixed to the bone when implanted. This may be accomplished by forming the plug with a geometry, e.g. an irregular surface, to which bone will attach or adhere to maintain the plug in a fixed position within the bone. Alternatively, a surface coating may be applied to the plug that fixes or stabilizes its position within the bone and does not permit movement of the plug relative to the bone. Surface coatings for this purpose include materials to which bone can readily attach such as tantalum, titanium, porous metal coatings such as Trabecular™, plasma sprayed titanium or tantalum, hydroxylapatite, or other coatings that provide a micro rough or porous surface with which tissue can integrate.

One or more radiopaque markers are also implanted into the cannulated bone implant. Implant markers may also be delivered into the implant using a needle or other instrument for this purpose. Implant markers may be delivered into the implant per se, by press fitting with a spacer in between markers in order to fix their position within the implant. Alternatively, the implant markers may be delivered into the implant embedded in a plug similar to the bone plug 10. The implant plug may be made from any biocompatible polymer, and may contain one or multiple radiopaque markers. The location of the markers within the implant plug is predetermined and the markers are fixed within the implant plug using injection molding or press-fitting techniques as described with the bone plug. In this way, the relative positions between markers in the bone and implant cannot change unless there is movement of the bone relative to the implant. The implant plug has a shape and diameter that allows it to fit into the canal of the target bone implant in a fixed position. As with the bone plug, the implant plug may be designed with a geometry that exerts sufficient friction on the canal of the implant on insertion to fix the position of the plug within the implant. A machined-locking mechanism, or other geometry that results in mechanical interference and locking may also be employed.

Figure 7:
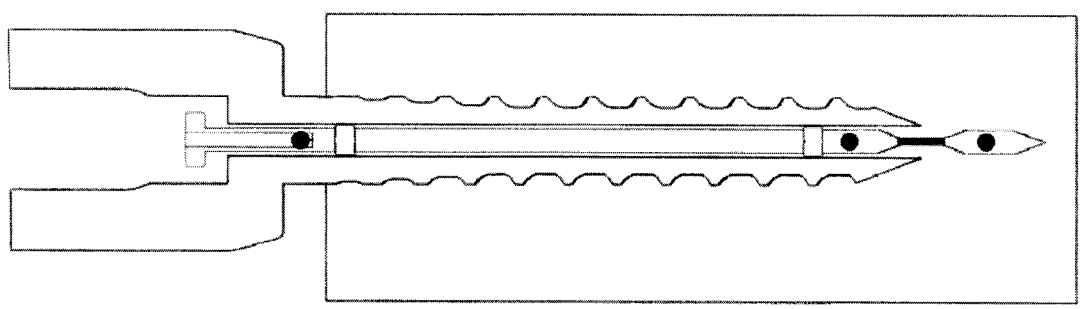
FIG. 7 illustrates implantation of another embodiment of a bone plug having a marker flexibly attached to its tip.

As with the bone plug, the implant plug may include variations. As indicated, the implant plug may include multiple markers in either a collinear or non collinear configuration. Markers in a non collinear arrangement in an implant plug provide a 3D representation of the implant, provided that the corresponding bone plug also includes markers with a non collinear configuration. The implant plug may additionally comprise a marker that is flexibly attached to an end of the plug, e.g. the anterior end, as shown in FIG. 7. Such an implant plug provides a means to introduce a marker into both the bone (e.g. the marker on the flexible attachment) and the implant at the same time.

The initial or first relative position of the bone marker(s) to the implant marker(s) may be determined radiographically under a first parameter using radiographic stereo photogrammetric analysis. Simultaneous exposures from two different perspectives may be obtained with a reference object for 3D reconstruction of the in vivo positioning of the markers. Planar x-rays may be used if motion exceeds measurement precision. Alternatively, the initial positioning of the bone and implant markers may be determined based on the known position of the implant.

A second relative position of the bone marker(s) to the implant marker(s) is determined radiographically under a second parameter. Movement between the bone implant and the bone can then be detected, if it occurs. Implant movement is detected if there is a change in the position of the bone marker relative to the implant marker from the first relative position to the second relative position, i.e. a change in the distance between the same two points on the bone and implant marker from the first relative position to the second relative position. Bone movement can also be detected by first ensuring no implant motion with the method described and then reconstructing the 3D bone motion from the combined movement of all markers.

The terms "first parameter" and "second parameter" are used herein to denote the condition(s) under which the first and second relative positions of bone marker(s) to implant marker(s) are determined. For example, in one scenario, the present method may be used to determine whether or not there is relative movement between bone and implant over a period of time. In this case, the first parameter for determining the first relative position would be a first or initial time, and the second parameter for determining the second relative position would be a subsequent or second time. In another scenario, the present method may be used to determine whether or not relative movement between bone and implant is induced in different loading states, e.g. a first loading state or position and a second loading state or position. For example, the first loading state may be a standing position while the second loading state may be a lying position, or the first loading state may be in a position with weight on the subject bone while the second loading position may be a position without weight on the subject bone.

Figure 3:
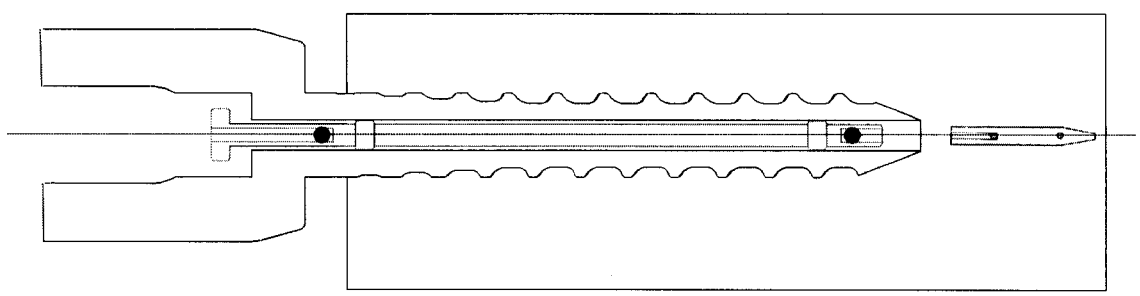
FIG. 3 illustrates alignment of markers on a bone plug and an implant plug on insertion.
Figure 4:
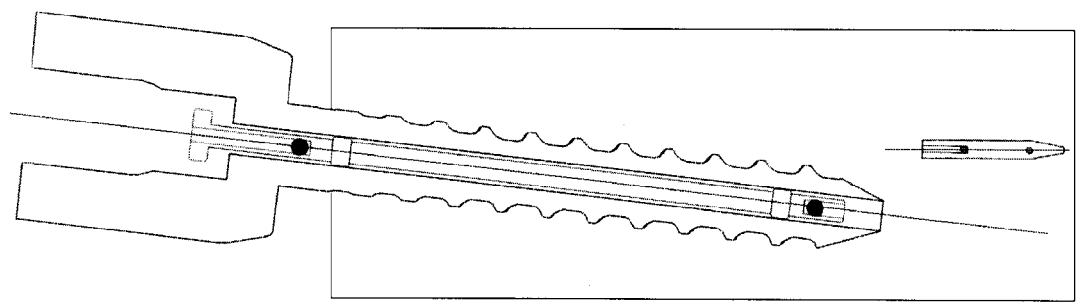
FIG. 4 illustrates lack of alignment of bone and implant plug markers on movement of an implant.
Figure 5:
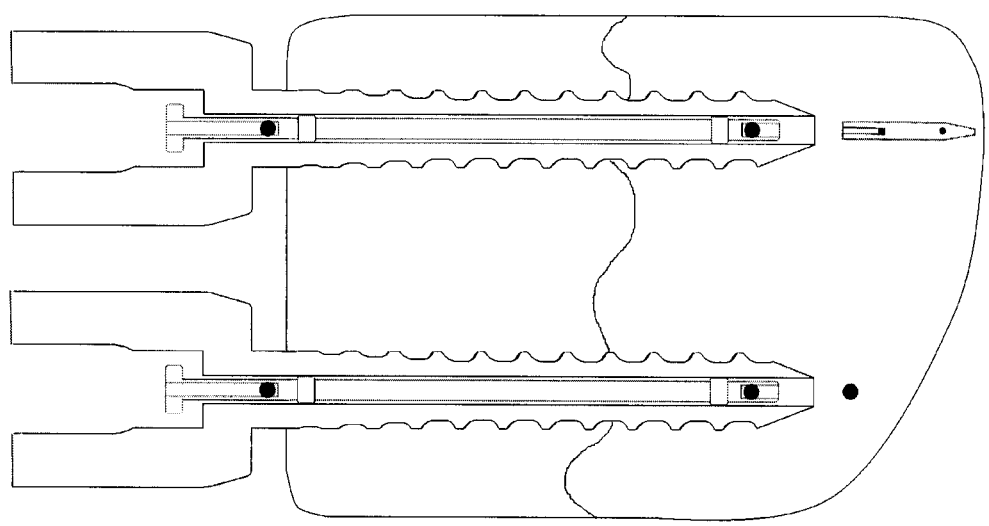
FIG. 5 illustrates a pair of bone implants including implant plug with markers, one in conjunction with a bone plug marker and one in conjunction with a bone marker (no plug)

Thus, to confirm that a bone implant is not moving, e.g. is not loose or migrating, within a bone, bone and implant markers introduced as described above, are utilized. The bone marker(s) and implant marker(s) are introduced in such a way that the positions of these markers are known and fixed in relation to each other, e.g. the bone and implant markers are implanted within a straight canal (e.g. which may have previously been formed by a guidewire used during the bone implant procedure) as shown in FIG. 3. First and second positions of the bone and implant markers relative to one another is determined under different parameters. Determination that the implant markers relative to the bone markers are not aligned based on the determination of the first and second positions as shown in FIG. 4 is evidence that the implant has moved.

The present method provides many benefits. Using the present method, no modification of the implant (e.g. such as a cannulated screw) is required. The position of the implant compared to the bone may be assessed using different parameters, e.g. time or loading states. Any relative changes in position of implant markers versus bone markers at different parameters represents implant migration. The initial positioning of bone and implant markers is established on insertion, using the methods described above. Thus, there is no need to radiographically assess the initial position. Therefore, to assess marker positions, only a single radiographic assessment at a subsequent time when the investigation of implant migration is desired is required. This provides the advantage of less radiation exposure to the patient as compared with traditional methods of determining implant migration.

Additionally, using the present bone and implant markers, planar or stereographic measurements can be made depending on the required level of accuracy. The implant and bone plugs comprise embedded markers which are a known distance apart. This allows for correction of perspective error in the case of planar assessments. Using RSA, exact relative 3D changes of the implant to the bone may be determined.

The present methodology may also be utilized to determine relative movement between different bones or at different sites within the same bone. If no implant migration is determined between bone and implant markers, then the bone markers can be combined with the implant markers to represent the bone in the determination of bone movement. Thus, the position of bone and implant markers at a first bone site and a second bone site (which may be on a different bone than the first bone site or the same bone) may be determined under a first parameter to provide the first relative position of the first and second bone sites. The second relative positioning at the first and second bone sites can then be determined under a second parameter, and a comparison of the first and second relative positions to determine if there was movement between the first and second bone sites. For example, in vertebrae fusion procedures, screws (implants) are fixed to adjacent vertebrae. If bone and implant markers associated with each vertebrae are determined not to move relative to one another, then the bone and implant markers for each vertebrae are representative of the position of the vertebrae. The relative positioning of the bone and implant markers for each vertebrae can be determined at different parameters to determine movement between the two adjacent vertebrae. The combined use of the bone and implant markers to represent each vertebrae advantageously enhances the accuracy of the determination.

It may be important in different clinical situations to determine if one marked implant is moving relative to another marked implant (bone plate, intermedullary nail, etc.), whether cannulated or solid. Thus, in another aspect, a method of determining relative motion measurements between first and second implants is provided in which a first position of first and second implants both including an embedded marker(s) is determined under a first parameter, and a second position of first and second implants is determined under a second parameter, and the positions are compared. A change in the distance of the markers in the first and second implants between the first and second positions is indicative of implant movement.

We claim:

1. A method of measuring the relative position of a bone implant within a bone in a patient to detect movement between the implant and bone, said method comprising the steps of:
    i) implanting a radiopaque bone marker into the bone, said bone marker having a first radiolucency detectable with medical imagery;
    ii) implanting the bone implant into the bone, said bone implant having a radiopaque implant marker inserted thereinto, said implant marker having a second radiolucency detectable with medical imagery;
    iii) using medical imagery to determine a first relative position of the bone marker to the implant marker for use as a first reference point;
    iv) applying a load to the bone;
    v) using medical imagery to determine a second relative position of the bone marker to the implant marker for use as a second reference point; and
    vi) determining a distance between the first reference point and the second reference point;
    wherein a distance greater than zero is indicative of movement of either the implant or the bone.

2. The method of claim 1, wherein steps iv) to vi) are repeated after a selected period of time.

3. The method of claim 1, wherein steps iv) to vi) are repeated in a series of spaced-apart time intervals.

4. The method of claim 1, wherein the patient is in a standing position during step iii), and is in a lying position during steps iv) to v).

5. The method of claim 1, wherein the patient is in a position with weight on the bone during step iii), and in a position without weight on the bone during steps iv) to v).

6. The method of claim 1, wherein the bone marker is introduced into the bone in a biocompatible bone plug, wherein the bone marker is in a fixed position within the bone plug.

7. The method of claim 1, wherein the implant marker is introduced into the implant in a biocompatible implant plug, wherein the implant marker is in a fixed position within the implant plug.

8. The method of claim 6, wherein the bone plug comprises a surface coating that stabilizes its position within the bone.

9. The method of claim 8, wherein the coating comprises one of tantalum and titanium.

10. The method of claim 1, wherein the bone marker and the implant marker are tantalum markers or titanium markers.

11. The method of claim 1, wherein more than one bone marker is implanted into the bone and/or more than one implant marker is implanted into the bone implant.

12. The method of claim 1, wherein the bone implant is a cannulated screw.

13. A method of measuring the relative position of a first bone site to a second bone site in a patient to detect movement between the two bone sites, said method comprising the steps of:
   i) implanting a first radiopaque bone marker into the first bone site, said first bone marker having a first radiolucency detectable with medical imagery;
   ii) implanting a first bone implant into the first bone site, said first bone implant having a first radiopaque implant marker inserted thereinto, said first implant marker having a second radiolucency detectable with medical imagery;
   iii) implanting a second radiopaque bone marker into the second bone site, said second bone marker having a third radiolucency detectable with medical imagery;
   iv) implanting a second bone implant into the second bone site, said second bone implant having a second radiopaque implant marker inserted thereinto, said second implant marker having a fourth radiolucency detectable with medical imagery;
   v) using medical imagery to determine a first relative position of the first bone implant and the first implant marker at the first bone site to the second bone marker and the second implant marker at the second bone site for use as a first reference point;
   vi) applying a load to the first bone site and the second bone site;
   vii) using medical imagery to determine
   a second relative position of the bone implant and the first implant marker at the first bone site to the second implant marker at the second bone site for use as a second reference point; and
   viii) determining a distance between the first reference point and the second reference point;
   wherein a distance greater than zero is indicative of movement of either the first bone implant or the second bone implant.

14. The method of claim 13, wherein steps vi) to viii) are repeated after a selected period of time.

15. The method of claim 13, wherein steps vi) to viii) are repeated in a sequence of spaced-apart time intervals.

16. The method of claim 13, wherein the first radiopaque bone marker is introduced into the first bone site in a first biocompatible bone plug wherein the first bone marker is in a fixed position within the first bone plug, and the second radiopaque bone marker is introduced into the second bone site in a second biocompatible bone plug wherein the second bone marker is in a fixed position within the second bone plug.

* * * * *